United States Patent [19]
Gremillet

[11] Patent Number: 5,834,218
[45] Date of Patent: Nov. 10, 1998

[54] BIOCHEMICAL SENSOR

[75] Inventor: Jacques Gremillet, Chevreuse, France

[73] Assignee: Thomson-CSF, Paris, France

[21] Appl. No.: 722,018

[22] PCT Filed: Feb. 16, 1996

[86] PCT No.: PCT/FR96/00257

§ 371 Date: Oct. 11, 1996

§ 102(e) Date: Oct. 11, 1996

[87] PCT Pub. No.: WO96/25513

PCT Pub. Date: Aug. 22, 1996

[30] Foreign Application Priority Data

Feb. 17, 1995 [FR] France .................................. 95 01829

[51] Int. Cl.⁶ ........................ G01N 33/552; G01N 33/569
[52] U.S. Cl. ........................ 435/7.31; 385/12; 385/129;
385/130; 422/55; 422/82.05; 422/82.08;
422/82.09; 422/82.11; 435/287.1; 435/287.2;
435/288.7; 435/808; 435/973; 436/464;
436/465; 436/518; 436/524; 436/527; 436/172;
436/805; 436/809
[58] Field of Search ........................... 385/12, 129, 130;
422/55, 57, 82.05, 82.08, 82.09, 82.11;
435/7.31, 287.1, 287.2, 288.7, 808, 973;
436/518, 524, 527, 164, 165, 172, 805,
809

[56] References Cited

U.S. PATENT DOCUMENTS

| | | |
|---|---|---|
| 3,510,806 | 5/1970 | Gremillet . |
| 4,931,384 | 6/1990 | Layton et al. .......................... 435/805 |
| 4,935,345 | 6/1990 | Guilbeau et al. .......................... 435/4 |
| 5,175,597 | 12/1992 | Cachier et al. . |
| 5,478,527 | 12/1995 | Gustafson et al. ................... 422/82.11 |

*Primary Examiner*—Christopher L. Chin
*Attorney, Agent, or Firm*—Oblon, Spivak, McClelland, Maier & Neustadt, P.C.

[57] ABSTRACT

The invention relates to a biochemical sensor including a substrate on which yeast cells are deposited which are capable of capturing one type of molecules (M) and of producing a chemical entity (P) at the outcome of the capture; it also includes means for detecting the entity (P). The yeast cells employed are yeast cells obtained by genetic manipulation, in which the capture sites have been adapted to the type of molecules (M).

8 Claims, 2 Drawing Sheets

BIOCHEMICAL SENSOR

BACKGROUND OF THE INVENTION

1. Field of the Invention

The field of the invention is that of molecular sensors capable of recognizing molecules specifically and of detecting them in very low concentrations.

2. Discussion of the Background

Sensors of this type are found to be particularly advantageous in fields as varied as the detection and identification of war gases, of diverse pollution, of narcotics, of perfume, etc., when what is being investigated is the presence of specific molecules, regardless of whether their architecture is simple or particularly sophisticated.

The characteristics of such sensors are chiefly the ability to recognize a type of molecule and the possibility of amplifying this molecular recognition so as to detect information that is sufficient to be capable of being utilized.

At the present time there are already sensors operating on the use of antibodies (for specific recognition) and of enzyme amplification processes for the transmission of information.

To give an example, some tests for tracking down molecules operate according to the following principle:

A specific antibody ($AB_1$) for the molecule to be detected is bound onto a membrane; the combination is immersed in a solution containing molecules to be detected (J), permitting the pairing of the antibody ($AB_1$) and of the molecule (J), the pairing being performed at a specific place in the said molecule. In a second step the $AB_1$-(J) combination may be immersed in another solution containing another specific anti J antibody $AB_2$ which itself may be bound to an enzyme. The structure described in FIG. 1 is then obtained. This molecular grouping can transform an entity S into product P, via the enzyme, at a rate depending on the catalytic power of the enzyme. The enzyme amplification thus obtained enables a detectable quantity of product P to be produced even when the molecules to be sensed are in very low concentrations. Typically, an acidity, a basicity, a colour or any other physicochemical phenomenon can be revealed.

In this type of process two major disadvantages continue to exist in the case of the applications aimed at in the present patent application. In fact, this process is limited to detection in solution; moreover, it needs to be carried out in two steps.

To envisage the concept of biochemical sensors which are selective and capable of detecting very low concentrations of a molecule in an ambient medium, one scheme consists in employing an interface between the external medium and a reaction medium which is connected to a detector, this interface including various sites for capturing the targeted molecules and the enzyme amplification being conducted within the reaction medium.

The various capture sites must be capable of triggering the enzyme amplification process as soon as they have captured the molecules which it is intended to detect. They must therefore fulfil the following two functions: to capture selectively one type of molecules and to transmit the information of this capture to a reaction medium which generates for it, by enzyme amplification, a signal which is sufficient to the detector (transducer of chemical information into physical information).

To ensure these different functions, living cell environments have available transmembrane receptors incorporated within a membrane consisting of phospholipids. These transmembrane receptors consist of transverse members (typically proteins organized into a helix) joined together by molecular bridges, like those illustrated in FIGS. 2a and 2b. On each side of the membrane this combination produces a reception site whose steric form depends on the molecular bridges and on the relative position of the transverse members permitting, on the external medium side, the capture of one type of molecule (M) for which the transmembrane receptor is adapted, and transmitting the deformation associated with the capture into the reaction medium. This distortion at the site $s_1$ is capable of triggering within the cell medium a whole process of reactions, in particular via enzymes which are present in the medium.

More precisely, it is known that the process of reproduction of some cells by mitosis (indirect cell division into identical cells) is perturbed when certain messenger molecules are captured. Thus, during the capture of molecules via transmembrane receptors it is possible to modify the intracellular mechanisms so as to activate some proteins at the genes which are active in respect of cell reproduction.

Furthermore, among known microorganisms, yeast cells appear to be very good candidates for producing biochemical sensors, because of their low cost, their robustness when compared with other living cells whose maintenance in a functional state presents problems, and, above all, by virtue of the present knowledge of their genotype.

SUMMARY OF THE INVENTION

Accordingly, the subject of the invention is a biochemical sensor based on yeast cells whose genotype has been modified so that the said yeast cells are capable of capturing a certain type of molecules and, at the outcome of this capture, they give rise to detectable information.

More precisely, the invention proposes a biochemical sensor characterized in that it includes:

a substrate on which yeast cells are deposited which are capable of capturing one type of messenger (M) and of producing a chemical entity (P) at the outcome of this capture;

means for detecting the chemical entity produced.

The chemical entity produced may advantageously be an optically recognizable protein. The means of detection may be of the optical density measurement, fluorescence measurement, light polarization measurement or similar type.

The substrate is a nutrient medium allowing the yeast cells to reproduce.

It may be advantageously an anhydrous gel filled with minerals, with sugar, and the like, on which the yeast cells are deposited and are subsequently activated by moistening.

BRIEF DESCRIPTION OF THE DRAWINGS

The invention will be understood better and other advantages will appear on reading the description which is to follow and by virtue of the attached figures, among which.

DETAILED DESCRIPTION OF THE PREFERRED EMBODIMENTS

Figure 1:
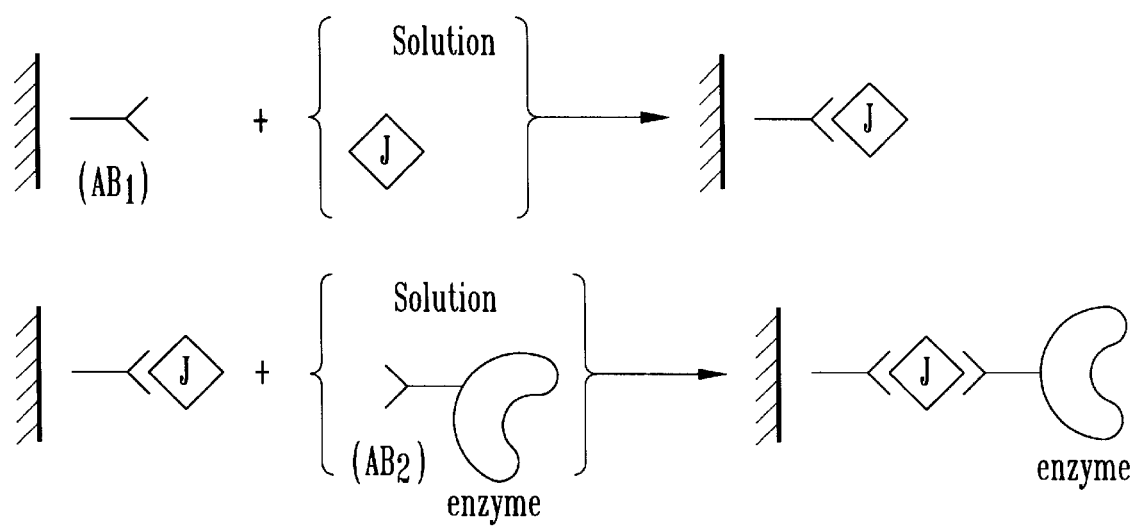
FIG. 1 illustrates a reaction scheme employed in a test for tracking down molecules in solution, according to the known art.
Figure 2A:
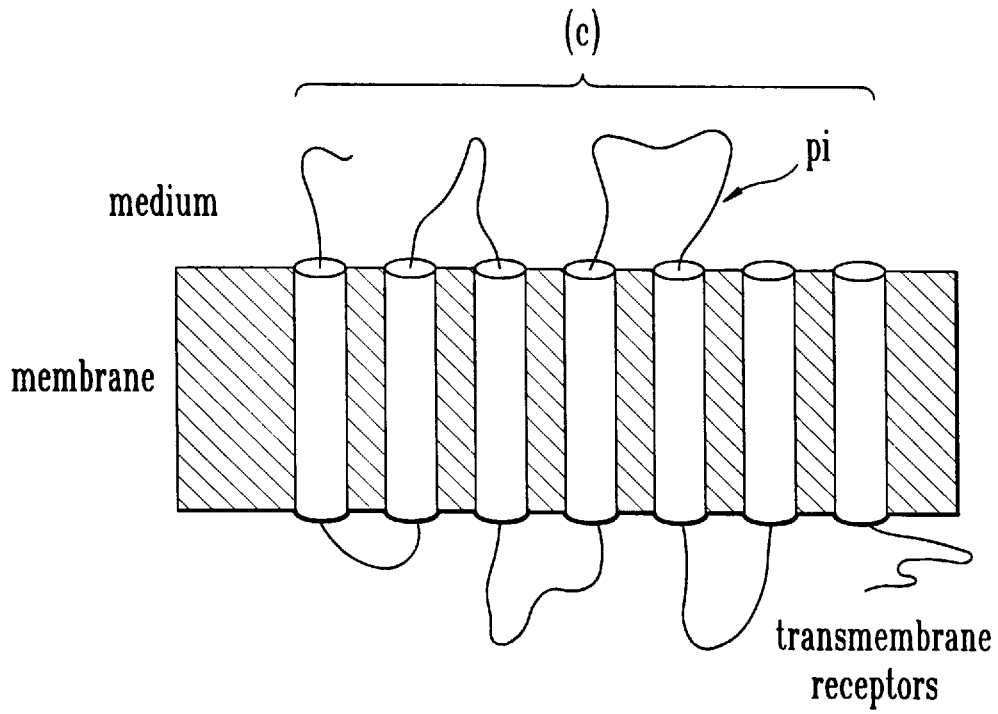
FIG. 2a shows diagrammatically a sectional view of a transmembrane receptor.
Figure 2B:
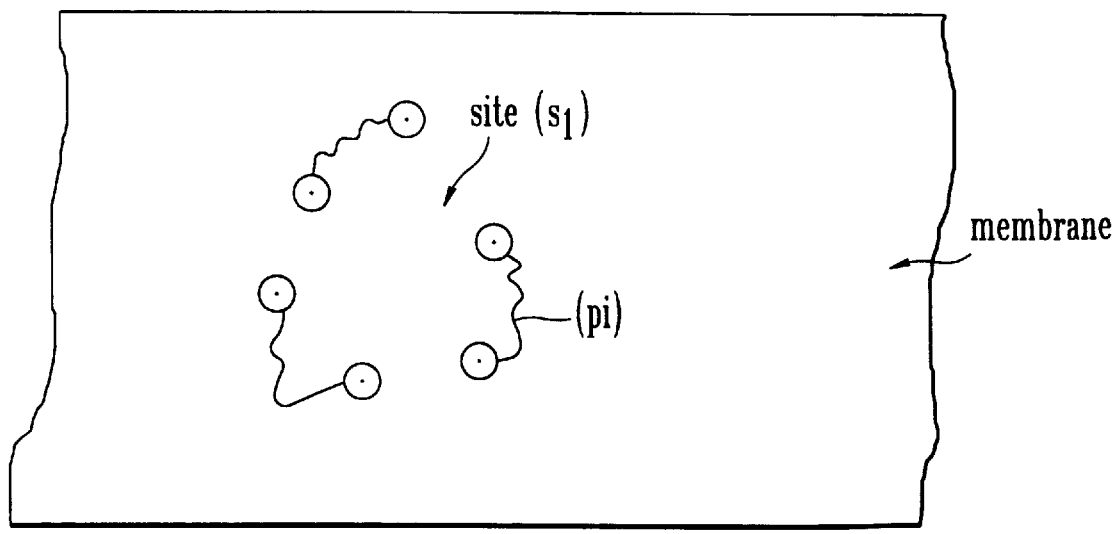
FIG. 2b shows diagrammatically a top view of a transmembrane receptor.

The biochemical sensor according to the invention includes a sensitive detection layer produced from the deposition of cells whose genotype has been modified. These genetic modifications can be performed by mutagenesis and/or by genetic engineering techniques, followed by a selection, among the cells obtained, of cells which are sensitive to a given chemical compound (or to a range of compounds). It is thus possible to lure a yeast cell whose reproduction by mitosis can be stopped when a very particular type of molecules is captured and also to stop this reproduction process via the capture of another type of molecule.

Mutagenesis is a natural process which consists of the random modification of some genes. This natural process can be accelerated especially by heating and this can be done a very large number of times in order to cause natural genetic mutations with a view to obtaining new transmembrane receptors which are adapted for the capture of targeted molecules.

The yeast cells employed in the biochemical sensor according to the invention preferably have not only been lured with a view of being made sensitive to different types of molecules, but they have also been lured to make them capable of producing a particular detectable entity showing evidence of the capture of targeted molecules.

At the present time the genome, the combined genotype, of the yeast cells is being controlled better and better; it thus becomes possible, by identifying the genes and their functions, to perturb this genotype by genetic manipulation, in order to change some of its characteristics. It is thus possible to insert certain members into this genotype, making it possible to adapt the transmembrane receptors to different types of molecules. The capture of a type of given molecule can, in its turn, trigger a whole series of specific chemical reactions leading to the specific appearance of a protein in particular. This protein may be selected for its optical properties.

Thus, by performing a whole series of tests, yeast cells are isolated whose genetic manipulation has resulted in the yeast cell being sensitized to molecules other than those which are naturally capable of being captured and has additionally resulted in the production of a specific entity.

These experiments can be performed and adapted to different types of molecules (M) so as to have available a series of sensors based on yeast cells responding specifically to molecules (Mi) with production, identical or otherwise, of entity (P) to be detected.

The sensor according to the invention may, more generally, identify a whole series of molecules (M) when it results from the association of N elementary biological sensors, each being designed to recognize a precise type of molecules (Mi).

By way of example, it is possible to produce a mosaic of N elementary sensors which are capable of producing the same coloured protein when they capture a molecule (Mi). Thus, by analysing the whole of the response of such a sensor it is possible to arrive at the identification of specific molecules which are present in a medium.

I claim:

1. Biochemical sensor characterized in that it comprises:
   a substrate on which yeast cells are deposited which are capable of capturing one type of molecules (M) and of producing a chemical entity (P) at the outcome of this capture;
   means for detecting the chemical entity (P) produced.

2. Biochemical sensor according to claim 1, characterized in that the yeast cells are yeast cells obtained by mutagenesis, wherein the mutagenesis causes the yeast cells to contain capture sites capable of capturing the type of molecules (M).

3. Biochemical sensor according to claim 1, characterized in that the yeast cells are yeast cells obtained by genetic manipulation of the genotype of said cells so as to adapt the capture sites of said cells to one type of molecules (M).

4. Biochemical sensor according to claim 1, wherein the substrate is a gel filled with sugar and inorganic salts.

5. Biochemical sensor according to claim 1, wherein the substrate is filled with yeast cells, and the substrate can be activated by moistening.

6. Biochemical sensor according to claim 1, wherein the entity (P) is a protein.

7. Biochemical sensor according to claim 1, wherein the biochemical sensor further comprises a physical means of detection which are optical means for measuring optical density, change in light polarization or fluorescence.

8. Biochemical sensor characterized in that it comprises a mosaic of elementary biochemical sensors according to claim 1, each elementary sensor being capable of detecting one type of molecule (Mi), the combination of the responses supplied by the means of detections ($m_i$) of each sensor making it possible to identify molecules present in a medium.

* * * * *